May 9, 1972 H. C. SWIM ET AL Plant Pat. 3,163
ROSE PLANT
Filed Sept. 29, 1970
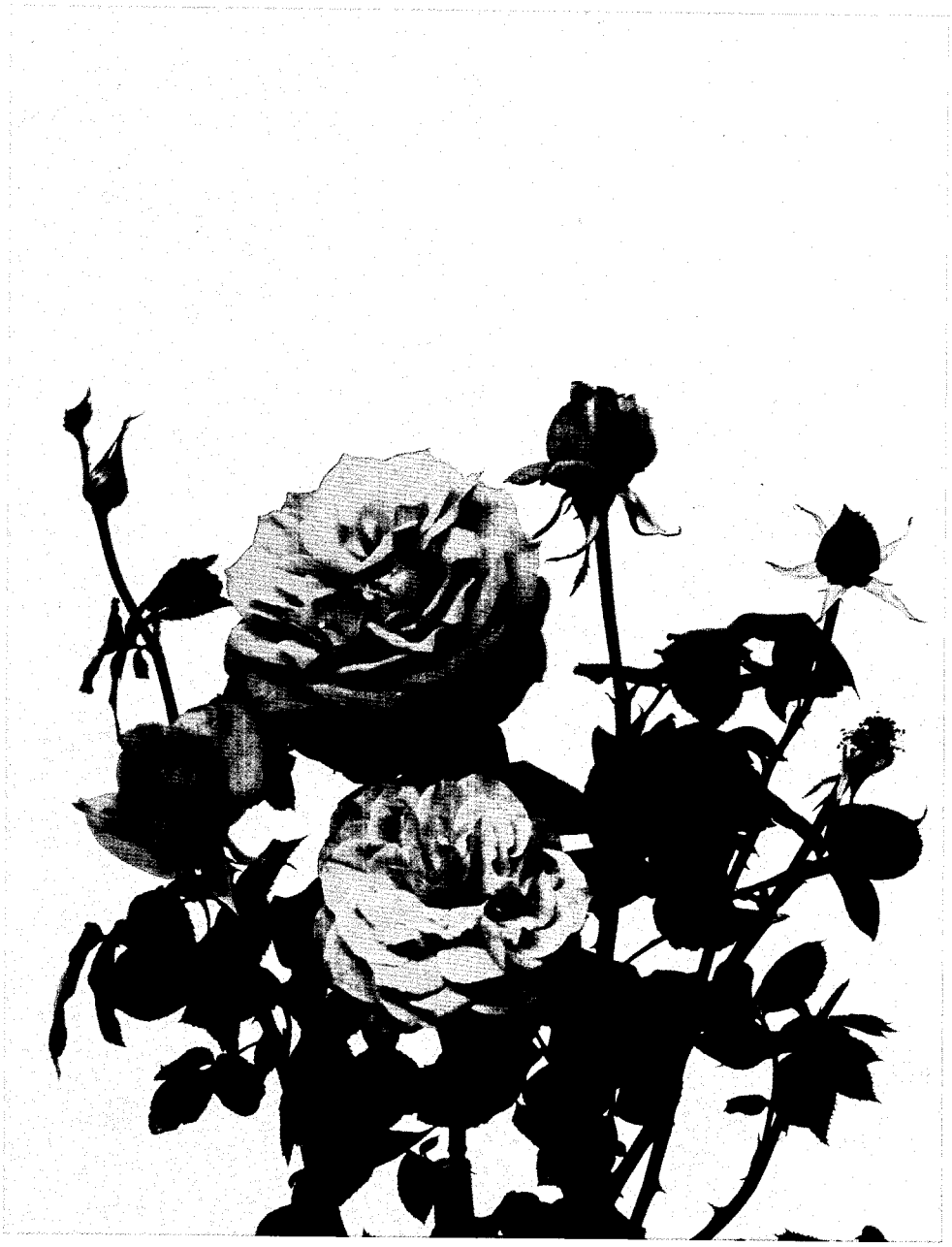
Inventors.
H. C. Swim
O. L. Meeks
By: Robb & Robb
Attorneys.

United States Patent Office

Plant Pat. 3,163
Patented May 9, 1972

3,163
ROSE PLANT

Herbert C. Swim and O. L. Weeks, Ontario, Calif., assignors to The Conard-Pyle Company, West Grove, Pa.

Filed Sept. 29, 1970, Ser. No. 76,650
Int. Cl. A01h 5/00
U.S. Cl. Plt.—20 1 Claim The present invention relates to a new and distinct variety of rose plant of the hybrid tea class, which was originated by us by crossing an unnamed and unpatented rose seedling derived from a cross of ["Happiness" (Plant Patent No. 911) × "Chrysler Imperial" (Plant Patent No. 1,167] × "El Capitan" (Plant Patent No. 1,796), with the variety "Comanche" (Plant Patent No. 2,855), said unnamed seedling being the seed parent and "Comanche" being the pollen parent.

As the result of this breeding, we have produced a new and improved rose variety which is distinguished from its parents, as well as from all other rose varieties of which we are aware, as evidenced by the following unique combination of characteristics which are outstanding in the new variety:

(1) A healthy and vigorous plant habit;
(2) Long and strong cutting stems which give good support to the blooms;
(3) Abundant foilage of excellent quality and having better than average disease resistance;
(4) A free blooming habit which results in good garden color almost constantly during its normal blooming season;
(5) Excellent flower petal substance, with consequent good qualities for cut flowers, as well as for garden and landscape use; and
(6) An attractive and distinctive fiery orange-red flower color which intensifies in its luminescence in hot weather.

In comparison with its unnamed seed parent, our new variety is more vigorous and more upright in plant habit and bears larger and darker green leaves which are more rounded in form, and its orange-red flower color has a fiery fluorescence which is not found in the dark velvety red flower color of the seed parent.

As compared with its pollen parent "Comanche," the new variety is more vigorous and more upright, although full and well-branched, in habit; its foliage is considerably improved in size, substance and color; its canes are green rather than brownish-green like those of "Comanche"; the flower buds are not as long, nor the open flowers as high-centered as those of "Comanche," but are far more luminescent and are a fiery orange-red color; the flowers have more substance and are more lasting both on the bush and as cut flowers; and while the flower petals of the new variety are not as large as those of "Comanche," the new variety is more floriferous, and the petal conformation in the open blooms is more regular and more consistent in flower form.

Asexual reproduction of our new variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Hardy; tall; outdoor; seedling; for cut flowers and for garden decoration.
Class: Hybrid tea.
Breeding: Seedling.
*Seed parent.*—An unnamed seedling of ["Happiness" × "Chrysler Imperial"] × "El Capitan."
*Pollen parent.*—"Comanche."
Propagation: Holds its distinguishing characteristics through succeeding propagations by budding.

*Flowers*

Locality where grown and observed: Chino, Calif.
Flowers borne: Singly; on strong, long stems.
Quantity of bloom: From free to abundant, both outdoors and in greenhouse.
Continuity: From intermittant to continuous.
Fragrance: From slight to moderate. Nature—spicy.
Bud:
*Peduncle.*—Short; from medium to heavy caliper; erect; stiff; almost smooth; few, if any, green prickles. Color—medium reddish-green.
*Before calyx breaks.*—Size—from small to medium. Form—short; oval; with some foliaceous appendages on the surface of the bud; with slender bristle-like foliaceous parts extending beyond the tip of the bud equal to ¾ or more of its length.
*As calyx breaks.*—Color—dark orange-red.
*As first petal opens.*—Size—from small to medium. Form—short; ovoid. Color—outside—somewhat darker than Dark Red, Hue 2.5 R 3/7—inside—somewhat darker than Dark Red, Hue 2.5 R 3/7.
*Opening.*—Opens up well.
Bloom:
*Size (when fully open).*—From medium to large; from 3 inches to 5 inches.
*Petalage.*—Double; from 32 to 36 petals; arranged regularly.
*Form.*—High-centered at first, but becoming cupped; petals being at first tightly cupped and rolled inward, but later becoming loosely cupped and rolled outward at maturity.
Petals:
*Texture.*—Thick and somewhat leathery.
*Appearance.*—Inside—somewhat shiny. Outside—velvety.
*Shape.*—Outside—broadly round; obovate; with apex broadly round. Intermediate—obovate; with apex broadly round. Inside—obovate; with apex broadly round.

This description of a newly opened flower was made from a rose grown outdoors during the month of October at Ontario, Calif.

*Color.*—*Outer petal*—Outside surface—Strong Red, Hue 5 R 4/12, but much more luminous, with a minute area of Brilliant Greenish Yellow, Hue 7.5 Y 9/8 at basal tip of petal. Inside surface—from Deep Purplish Red, Hue 10 R P 3/10 to Strong Red, Hue 5 R 4/12, but much more luminous, with a minute area of Vivid Greenish Yellow, Hue 7.5 Y 8/12 at basal tip of petal. *Intermediate petal*—outside surface—Deep Purplish Red, Hue 10 R P 3/10, but much more luminous, with a minute area of Brilliant Greenish Yellow, Hue 7.5 Y 9/8 at basal tip of petal. Inside surface—from Deep Purplish Red, Hue 10 R P 3/10 to Strong Red, Hue 5 R 4/12, but much more luminous, with a minute area of Vivid Greenish Yellow, Hue 7.5 Y 8/12 at basal tip of petal. *Inner petal*—outside surface—Deep Purplish Red, Hue 10 R P 3/10, but much more luminous, with a minute area of Brilliant Greenish Yellow, Hue 7.5 Y 9/8 at basal tip of petal. Inside surface—from Deep Purplish Red, Hue 10 R P 3/10 to Strong Red, Hue 5 R 4/12, but much more luminous, with a minute area of Vivid Greenish Yellow, Hue 7.5 Y 8/12 at basal tip of petal.

This description was made from a rose that was open for three days outdoors during the month of October at Ontario, Calif.

*Color.—Outer petal*—Outside surface—Strong Red, Hue 5 R 4/12, blending to Dark Reddish Orange, Hue 7.5 R 4/11, but more luminous, with a minute area of Brilliant Greenish Yellow, Hue 7.5 Y 9/8 at basal tip of petal. Inside surface—Strong Red, Hue 5 R 4/12, but more luminous, with a minute area of Vivid Greenish Yellow, Hue 7.5 Y 8/12 at basal tip of petal. *Inner petal*—outside surface—from Strong Red, Hue 5 R 4/12 to Strong Reddish Orange, Hue 7.5 R 5/13, but more luminous, with a minute area of Brilliant Greenish Yellow, Hue 7.5 Y 9/8 at basal tip of petal. Inside surface—Strong Red, Hue 5 R 4/12, blending to darker but more luminous, with a minute area of Vivid Greenish Yellow, Hue 7.5 Y 8/12 at basal tip of petal.

*General color effect.*—Newly opened flower—brightly luminous red, blending to luminous fiery orange-red. 3-days open—a more glowing fiery red, continuing its blending to a glowing orange-red.

*Behavior*—Drops off cleanly; fading reddish purple; the fiery brightness of the orange-red color of open flower is intensified by hot, dry weather.

*Flower longevity.*—On bush in garden—5 days or more in growing season. Cut roses grown outdoors and kept at living room temperatures—4 or 5 days in growing season.

*Reproductive organs*

Stamens: Many; arranged irregularly about pistils; tucked in calyx.

Filaments: From about short to medium length; few with anthers. Color—reddish.

Anthers: Medium size; all open at once. Color—from reddish-yellow to yellow.

Pollen: Very sparse. Color—from white to lemon yellow.

Pistils: Medium number.

Styles: Very uneven; from short to medium length; medium caliper; loosely separated.

Stigma: Color—White.

Ovaries: All protruding from calyx.

Hips: None observed.

Sepals: Falling soon; moderately long; spear-shaped curled. Color—reddish green.

Seeds: None observed.

*Plant*

Foliage:

*Leaves.*—Compound of 3–5 leaflets; very abundant; moderately large size; moderately soft to heavy; semi-glossy.

*Leaflets.*—Shape—ovoid. Apex—acuminate. Base—obtuse. Margin—serrate.

*Color.*—Mature—upper surface—moderately dark green. Under surface—from moderately light green to bronze-red. Young—upper surface—reddish-green. Under surface—moderately light red.

*Rachis (the supporting stem of the compound leaf).*—Medium weight. Upper side—smooth. Under side—smooth.

*Stipules.*—From moderately short to medium length; moderately narrow; with moderately medium to long points turning out at an angle of more than 45°; recurved occasionally toward the stem.

*Disease resistance.*—Above average resistance to powdery mildew, as determined by comparison with other rose varieties grown under comparable conditions at Ontario, Calif.

Growth:

*Habit.*—Tall; bushy; upright; much-branched.

*Growth.*—Very free; vigorous.

*Canes.*—From medium to heavy caliper.

*Main stems.*—Color—light green. *Large prickles*—several; medium long; straight; with narrow, oblong base. Color—light green. *Small prickles*—Few. Color—Brown. *Hairs*—None.

*Branches.*—Color—light green. *Large prickles*—from few to several; medium long; hooked downward; with narrow base. Color—light green.

*Small prickles*—few. Color—green. *Hairs*—None.

*New shoots.*—Color—greenish red. *Large prickles*—very few; short; hooked downward; with short, narrow base. Color—greenish red. *Small prickles*—few. Color—reddish. *Hairs*—None.

We claim:

1. A new and distinct variety of rose plant of the hybrid tea class, substantially as herein shown and described, characterized particularly as to novelty by the unique combination of a healthy and vigorous plant habit, long and strong cutting stems which give good support to the blooms, abundant foliage of excellent quality and having better than average disease resistance, a free blooming habit which results in good garden color almost constantly during its normal blooming season, excellent flower petal substance, with consequent good qualities for cut flowers, as well as for garden and landscape use, and an attractive and distinctive fiery orange-red flower color which intensifies in its luminescence in hot weather.

No references cited.

ROBERT E. BAGWILL, Primary Examiner